(12) United States Patent
Tiwari et al.

(10) Patent No.: US 8,722,736 B2
(45) Date of Patent: May 13, 2014

(54) MULTI-DOSE CONCENTRATE ESMOLOL WITH BENZYL ALCOHOL

(75) Inventors: Deepak Tiwari, Raritan, NJ (US); George Owoo, North Plainfield, NJ (US); Rekha Nayak, Monmouth Junction, NJ (US); Kenneth E. Burhop, Spring Grove, IL (US)

(73) Assignees: Baxter International Inc., Deerfield, IL (US); Baxter Healthcare SA, Glattpark (Opfikton) (CH)

( * ) Notice: Subject to any disclaimer, the term of this patent is extended or adjusted under 35 U.S.C. 154(b) by 0 days.

(21) Appl. No.: 11/752,103

(22) Filed: May 22, 2007

(65) Prior Publication Data

US 2008/0293810 A1 Nov. 27, 2008

(51) Int. Cl.
*A61K 31/24* (2006.01)

(52) U.S. Cl.
USPC .......................................... 514/538

(58) Field of Classification Search
None
See application file for complete search history.

(56) References Cited

U.S. PATENT DOCUMENTS

| | | | |
|---|---|---|---|
| 2,525,071 A | 10/1950 | Hardy et al. | |
| 2,720,203 A | 10/1955 | Burns et al. | |
| 2,745,785 A | 5/1956 | Bruce et al. | |
| 3,685,261 A | 8/1972 | McIlvaine et al. | |
| 4,056,635 A | 11/1977 | Glen et al. | |
| 4,073,943 A | 2/1978 | Wretlind et al. | |
| 4,340,589 A | 7/1982 | Uemura et al. | |
| 4,387,103 A | 6/1983 | Erhardt et al. | |
| 4,452,817 A | 6/1984 | Glen et al. | |
| 4,540,602 A | 9/1985 | Motoyama et al. | |
| 4,593,119 A | 6/1986 | Erhardt et al. | |
| 4,606,940 A | 8/1986 | Frank et al. | |
| 4,608,278 A | 8/1986 | Frank et al. | |
| 4,622,219 A | 11/1986 | Haynes | |
| 4,725,442 A | 2/1988 | Haynes | |
| 4,786,735 A | 11/1988 | Graboyes et al. | |
| 4,798,846 A | 1/1989 | Glen et al. | |
| 4,826,689 A | 5/1989 | Violante | |
| 4,857,552 A | 8/1989 | Rosenberg et al. | |
| 4,973,465 A | 11/1990 | Baurain et al. | |
| 4,997,454 A | 3/1991 | Violante et al. | |

(Continued)

FOREIGN PATENT DOCUMENTS

| | | |
|---|---|---|
| EP | 0169618 | 1/1986 |
| EP | 0207134 | 1/1987 |

(Continued)

OTHER PUBLICATIONS

Akers; "Chapter 41: Parenteral Preparations"; 2006; Remington: The Science and Practice of Pharmacy; 21st Ed.; pp. 802-804.*

(Continued)

*Primary Examiner* — Timothy Thomas
(74) *Attorney, Agent, or Firm* — Marshall, Gerstein & Borun LLP

(57) ABSTRACT

Disclosed are concentrate esmolol injection essentially free from other related esters of esmolol and diluted esmolol compositions. The concentrate esmolol formulation includes from about 25-1000 mg/ml of esmolol and about 1-25% w/v of benzyl alcohol and the combination thereof. The compositions can also be used as multi-dose compositions. The present invention also discloses diluted, ready-to-use compositions of esmolol prepared by dilution of the present invention concentrates. Also disclosed are methods of making and using the ready-to-use compositions of the present invention.

14 Claims, 1 Drawing Sheet

Esmolol Transesterification Reaction

(56) References Cited

U.S. PATENT DOCUMENTS

| | | |
|---|---|---|
| 5,017,609 A | 5/1991 | Escobar et al. |
| 5,023,271 A | 6/1991 | Vigne et al. |
| 5,049,322 A | 9/1991 | Devissaguet et al. |
| 5,078,994 A | 1/1992 | Nair et al. |
| 5,091,187 A | 2/1992 | Haynes |
| 5,091,188 A | 2/1992 | Haynes |
| 5,100,591 A | 3/1992 | Leclef et al. |
| 5,118,528 A | 6/1992 | Fessi et al. |
| 5,122,543 A | 6/1992 | Khanna et al. |
| 5,133,908 A | 7/1992 | Stainmesse et al. |
| 5,145,684 A | 9/1992 | Liversidge et al. |
| 5,151,264 A | 9/1992 | Samain et al. |
| 5,152,923 A | 10/1992 | Weder et al. |
| 5,171,566 A | 12/1992 | Mizushima et al. |
| 5,174,930 A | 12/1992 | Stainmesse et al. |
| 5,188,837 A | 2/1993 | Domb |
| 5,246,707 A | 9/1993 | Haynes |
| 5,250,236 A | 10/1993 | Gasco et al. |
| 5,269,979 A | 12/1993 | Fountain |
| 5,298,262 A | 3/1994 | Na et al. |
| 5,302,401 A | 4/1994 | Liversidge et al. |
| 5,306,519 A | 4/1994 | Peterson et al. |
| 5,314,506 A | 5/1994 | Midler, Jr. et al. |
| 5,318,767 A | 6/1994 | Liversidge et al. |
| 5,326,552 A | 7/1994 | Na et al. |
| 5,336,507 A | 8/1994 | Na et al. |
| 5,340,564 A | 8/1994 | Illig et al. |
| 5,346,702 A | 9/1994 | Na et al. |
| 5,352,459 A | 10/1994 | Hollister et al. |
| 5,354,563 A | 10/1994 | Toyotama et al. |
| 5,389,263 A | 2/1995 | Gallagher et al. |
| 5,399,363 A | 3/1995 | Liversidge et al. |
| 5,417,956 A | 5/1995 | Moser |
| 5,429,824 A | 7/1995 | June |
| 5,447,710 A | 9/1995 | Na et al. |
| 5,466,646 A | 11/1995 | Moser |
| 5,468,224 A | 11/1995 | Souryal |
| 5,470,583 A | 11/1995 | Na et al. |
| 5,474,989 A | 12/1995 | Hashimoto et al. |
| 5,494,683 A | 2/1996 | Liversidge et al. |
| 5,510,118 A | 4/1996 | Bosch et al. |
| 5,518,187 A | 5/1996 | Bruno et al. |
| 5,518,738 A | 5/1996 | Eickhoff et al. |
| 5,534,270 A | 7/1996 | De Castro |
| 5,543,133 A | 8/1996 | Swanson et al. |
| RE35,338 E | 9/1996 | Haynes |
| 5,552,160 A | 9/1996 | Liversidge et al. |
| 5,560,932 A | 10/1996 | Bagchi et al. |
| 5,560,933 A | 10/1996 | Soon-Shiong et al. |
| 5,565,383 A | 10/1996 | Sakai et al. |
| 5,569,448 A | 10/1996 | Wong et al. |
| 5,573,783 A | 11/1996 | Desieno et al. |
| 5,578,325 A | 11/1996 | Domb et al. |
| 5,580,579 A | 12/1996 | Ruddy et al. |
| 5,587,143 A | 12/1996 | Wong |
| 5,591,456 A | 1/1997 | Franson et al. |
| 5,605,785 A | 2/1997 | Texter et al. |
| 5,626,864 A | 5/1997 | Rosenberg et al. |
| 5,635,609 A | 6/1997 | Levy et al. |
| 5,637,568 A | 6/1997 | Orsolini et al. |
| 5,637,625 A | 6/1997 | Haynes |
| 5,641,515 A | 6/1997 | Ramtoola et al. |
| 5,641,745 A | 6/1997 | Ramtoola et al. |
| 5,660,858 A | 8/1997 | Parikh et al. |
| 5,662,883 A | 9/1997 | Bagchi et al. |
| 5,662,932 A | 9/1997 | Amselem et al. |
| 5,665,331 A | 9/1997 | Bagchi et al. |
| 5,665,383 A | 9/1997 | Grinstaff et al. |
| 5,679,576 A | 10/1997 | Kawai et al. |
| 5,707,634 A | 1/1998 | Schmitt |
| 5,716,642 A | 2/1998 | Bagchi et al. |
| 5,720,551 A | 2/1998 | Shechter |
| 5,766,635 A | 6/1998 | Spenleuhauer et al. |
| 5,780,062 A | 7/1998 | Frank et al. |
| 5,833,891 A | 11/1998 | Subramaniam et al. |
| 5,858,410 A | 1/1999 | Muller et al. |
| 5,862,999 A | 1/1999 | Czekai et al. |
| 5,874,111 A | 2/1999 | Maitra et al. |
| 5,874,574 A | 2/1999 | Johnston et al. |
| 5,885,486 A | 3/1999 | Westesen et al. |
| 5,885,984 A | 3/1999 | MacLeod et al. |
| 5,886,239 A | 3/1999 | Kudzma et al. |
| 5,916,583 A | 6/1999 | Broberg et al. |
| 5,916,596 A | 6/1999 | Desai et al. |
| 5,922,355 A | 7/1999 | Parikh et al. |
| 5,939,100 A | 8/1999 | Albrechtsen et al. |
| 5,981,719 A | 11/1999 | Woiszwillo et al. |
| 5,989,583 A | 11/1999 | Amselem et al. |
| 6,007,845 A | 12/1999 | Domb et al. |
| 6,039,981 A | 3/2000 | Woo et al. |
| 6,045,826 A | 4/2000 | Borowy-Borowski et al. |
| 6,045,829 A | 4/2000 | Liversidge et al. |
| 6,048,550 A | 4/2000 | Chan et al. |
| 6,063,138 A | 5/2000 | Hanna et al. |
| 6,063,910 A | 5/2000 | Debenedetti et al. |
| 6,068,858 A | 5/2000 | Liversidge et al. |
| 6,083,514 A | 7/2000 | Chang et al. |
| 6,086,376 A | 7/2000 | Moussa et al. |
| 6,090,925 A | 7/2000 | Woiszwillo et al. |
| 6,090,983 A | 7/2000 | Yokoyama et al. |
| 6,100,302 A | 8/2000 | Pejaver et al. |
| 6,132,750 A | 10/2000 | Perrier et al. |
| 6,139,870 A | 10/2000 | Verrecchia et al. |
| 6,143,211 A | 11/2000 | Mathiowitz et al. |
| 6,143,778 A | 11/2000 | Gautier et al. |
| 6,146,663 A | 11/2000 | Bissery et al. |
| 6,153,219 A | 11/2000 | Creeth et al. |
| 6,153,225 A | 11/2000 | Lee et al. |
| 6,165,506 A | 12/2000 | Jain et al. |
| 6,177,103 B1 | 1/2001 | Pace et al. |
| 6,197,757 B1 | 3/2001 | Perrier et al. |
| 6,207,134 B1 | 3/2001 | Fahlvik et al. |
| 6,207,178 B1 | 3/2001 | Westesen et al. |
| 6,214,384 B1 | 4/2001 | Pallado et al. |
| 6,217,886 B1 | 4/2001 | Onyuksel et al. |
| 6,221,332 B1 | 4/2001 | Thumm et al. |
| 6,221,398 B1 | 4/2001 | Jakupovic et al. |
| 6,221,400 B1 | 4/2001 | Liversidge et al. |
| 6,228,399 B1 | 5/2001 | Parikh et al. |
| 6,231,890 B1 | 5/2001 | Naito et al. |
| 6,235,224 B1 | 5/2001 | Mathiowitz et al. |
| 6,238,677 B1 | 5/2001 | Fanta et al. |
| 6,238,694 B1 | 5/2001 | Gasco et al. |
| 6,245,349 B1 | 6/2001 | Yiv et al. |
| 6,248,363 B1 | 6/2001 | Patel et al. |
| 6,261,537 B1 | 7/2001 | Klaveness et al. |
| 6,264,922 B1 | 7/2001 | Wood et al. |
| 6,267,989 B1 | 7/2001 | Liversidge et al. |
| 6,268,053 B1 | 7/2001 | Woiszwillo et al. |
| 6,270,806 B1 | 8/2001 | Liversidge et al. |
| 6,294,204 B1 | 9/2001 | Rossling et al. |
| 6,299,906 B1 | 10/2001 | Bausch et al. |
| 6,306,406 B1 | 10/2001 | Deluca |
| 6,310,094 B1 | 10/2001 | Liu et al. |
| 6,337,092 B1 | 1/2002 | Khan et al. |
| 6,344,271 B1 | 2/2002 | Yadav et al. |
| 6,346,533 B1 | 2/2002 | Cha et al. |
| 6,365,191 B1 | 4/2002 | Burman et al. |
| 6,375,986 B1 | 4/2002 | Ryde et al. |
| 6,387,409 B1 | 5/2002 | Khan et al. |
| 6,391,832 B2 | 5/2002 | Lyons et al. |
| 6,395,300 B1 | 5/2002 | Straub et al. |
| 6,428,814 B1 | 8/2002 | Bosch et al. |
| 6,458,387 B1 | 10/2002 | Scott et al. |
| 6,461,642 B1 | 10/2002 | Bisrat et al. |
| 6,462,093 B1 | 10/2002 | Miyamoto et al. |
| 6,528,540 B2 | 3/2003 | Liu et al. |
| 6,607,784 B2 | 8/2003 | Kipp et al. |
| 6,616,869 B2 | 9/2003 | Mathiowitz et al. |
| 6,667,048 B1 | 12/2003 | Lambert et al. |
| 6,682,761 B2 | 1/2004 | Pace et al. |
| 6,835,396 B2 | 12/2004 | Brynjelsen et al. |
| 6,869,617 B2 | 3/2005 | Kipp et al. |
| 6,884,436 B2 | 4/2005 | Kipp et al. |

(56) References Cited

U.S. PATENT DOCUMENTS

| | | |
|---|---|---|
| 7,763,469 B2 | 7/2010 | Babichenko et al. |
| 2001/0007678 A1 | 7/2001 | Baert et al. |
| 2001/0025058 A1 | 9/2001 | Borowy-Borowski et al. |
| 2001/0042932 A1 | 11/2001 | Mathiowitz et al. |
| 2002/0012675 A1 | 1/2002 | Jain et al. |
| 2002/0012704 A1 | 1/2002 | Pace et al. |
| 2002/0036776 A1 | 3/2002 | Shimaoka |
| 2002/0041896 A1 | 4/2002 | Straub et al. |
| 2002/0048610 A1 | 4/2002 | Cima et al. |
| 2002/0054912 A1 | 5/2002 | Kim et al. |
| 2002/0076347 A1 | 6/2002 | Maerz |
| 2002/0110599 A1 | 8/2002 | Auweter et al. |
| 2002/0127278 A1 | 9/2002 | Kipp et al. |
| 2002/0147239 A1 | 10/2002 | Liu et al. |
| 2002/0168402 A1 | 11/2002 | Kipp et al. |
| 2002/0182107 A1 | 12/2002 | Lagharn, Jr. et al. |
| 2003/0003155 A1 | 1/2003 | Kipp et al. |
| 2003/0031719 A1 | 2/2003 | Kipp et al. |
| 2003/0044433 A1 | 3/2003 | Werling et al. |
| 2003/0054042 A1 | 3/2003 | Liversidge et al. |
| 2003/0059472 A1 | 3/2003 | Brynjelsen et al. |
| 2003/0072807 A1 | 4/2003 | Wong et al. |
| 2003/0077329 A1 | 4/2003 | Kipp et al. |
| 2003/0096013 A1 | 5/2003 | Werling et al. |
| 2003/0100568 A1 | 5/2003 | Werling et al. |
| 2003/0170279 A1 | 9/2003 | Lambert et al. |
| 2003/0206959 A9 | 11/2003 | Kipp et al. |
| 2003/0211083 A1 | 11/2003 | Vogel et al. |
| 2004/0022861 A1 | 2/2004 | Williams et al. |
| 2004/0022862 A1 | 2/2004 | Kipp et al. |
| 2004/0043077 A1 | 3/2004 | Brown |
| 2004/0053375 A1 | 3/2004 | Tan et al. |
| 2004/0245662 A1 | 12/2004 | Chaubal et al. |
| 2004/0256749 A1 | 12/2004 | Chaubal et al. |
| 2005/0013868 A1 | 1/2005 | Brynjelsen et al. |
| 2005/0037083 A1 | 2/2005 | Brynjelsen et al. |
| 2005/0142199 A1 | 6/2005 | Tian et al. |
| 2005/0244503 A1 | 11/2005 | Rabinow et al. |
| 2007/0141090 A1 | 6/2007 | Harris et al. |

FOREIGN PATENT DOCUMENTS

| | | |
|---|---|---|
| EP | 0275796 | 7/1988 |
| EP | 0349428 | 1/1990 |
| EP | 0372070 | 6/1990 |
| EP | 0377477 | 7/1990 |
| EP | 0379379 | 7/1990 |
| EP | 0423697 | 4/1991 |
| EP | 0498482 | 8/1992 |
| EP | 0499299 | 8/1992 |
| EP | 0517565 | 12/1992 |
| EP | 0535534 | 4/1993 |
| EP | 0577215 | 1/1994 |
| EP | 0600532 | 6/1994 |
| EP | 0601618 | 6/1994 |
| EP | 0601619 | 6/1994 |
| EP | 0602700 | 6/1994 |
| EP | 0602702 | 6/1994 |
| EP | 0605024 | 7/1994 |
| EP | 0642992 | 3/1995 |
| EP | 0644755 | 3/1995 |
| EP | 0652011 | 5/1995 |
| EP | 0720471 | 7/1996 |
| EP | 0730406 | 9/1996 |
| EP | 0752245 | 1/1997 |
| EP | 0754034 | 1/1997 |
| EP | 0788350 | 8/1997 |
| EP | 0804162 | 11/1997 |
| EP | 0808154 | 11/1997 |
| EP | 0812187 | 12/1997 |
| EP | 0820300 | 1/1998 |
| EP | 0828479 | 3/1998 |
| EP | 0831770 | 4/1998 |
| EP | 0832569 | 4/1998 |
| EP | 0857484 | 8/1998 |
| EP | 0988863 | 3/2000 |
| EP | 1012204 | 6/2000 |
| EP | 1105109 | 6/2001 |
| EP | 1156788 | 11/2001 |
| EP | 1210942 | 6/2002 |
| EP | 1277724 | 1/2003 |
| EP | 1417962 A1 | 5/2004 |
| EP | 1652533 | 5/2006 |
| FR | 2817478 | 6/2002 |
| FR | 2838969 | 10/2003 |
| JP | 02306902 | 12/1990 |
| WO | WO-85/00011 | 1/1985 |
| WO | WO-86/08676 | 7/1986 |
| WO | WO-89/11850 | 12/1989 |
| WO | WO-89/11855 | 12/1989 |
| WO | WO-90/03782 | 4/1990 |
| WO | WO-90/15593 | 12/1990 |
| WO | WO-91/06292 | 5/1991 |
| WO | WO-91/07170 | 5/1991 |
| WO | WO-91/12794 | 9/1991 |
| WO | WO-91/16068 | 10/1991 |
| WO | WO-92/00731 | 1/1992 |
| WO | WO-92/03380 | 3/1992 |
| WO | WO-92/08447 | 5/1992 |
| WO | WO-92/17214 | 10/1992 |
| WO | WO-93/25190 | 12/1993 |
| WO | WO-94/07999 | 4/1994 |
| WO | WO-94/20072 | 9/1994 |
| WO | WO-95/05164 | 2/1995 |
| WO | WO-95/27482 | 10/1995 |
| WO | WO-95/33488 | 12/1995 |
| WO | WO-95/00567 | 1/1996 |
| WO | WO-96/14833 | 5/1996 |
| WO | WO-96/20698 | 7/1996 |
| WO | WO-96/24336 | 8/1996 |
| WO | WO-96/24340 | 8/1996 |
| WO | WO-96/25150 | 8/1996 |
| WO | WO-96/25152 | 8/1996 |
| WO | WO-96/25918 | 8/1996 |
| WO | WO-96/31231 | 10/1996 |
| WO | WO-97/03651 | 2/1997 |
| WO | WO-97/03657 | 2/1997 |
| WO | WO-97/14407 | 4/1997 |
| WO | WO-97/30695 | 8/1997 |
| WO | WO-97/36611 | 10/1997 |
| WO | WO-97/41837 | 11/1997 |
| WO | WO-97/44014 | 11/1997 |
| WO | WO-98/01162 | 1/1998 |
| WO | WO-98/07410 | 2/1998 |
| WO | WO-98/07414 | 2/1998 |
| WO | WO-98/14170 | 4/1998 |
| WO | WO-98/14174 | 4/1998 |
| WO | WO-98/14180 | 4/1998 |
| WO | WO-98/24450 | 6/1998 |
| WO | WO-98/31346 | 7/1998 |
| WO | WO-98/35666 | 8/1998 |
| WO | WO-98/47492 | 10/1998 |
| WO | WO-98/56362 | 12/1998 |
| WO | WO-98/57967 | 12/1998 |
| WO | WO-99/00113 | 1/1999 |
| WO | WO-99/02665 | 1/1999 |
| WO | WO-99/03450 | 1/1999 |
| WO | WO-99/06022 | 2/1999 |
| WO | WO-99/39696 | 2/1999 |
| WO | WO-99/16443 | 4/1999 |
| WO | WO-99/29316 | 6/1999 |
| WO | WO-99/30833 | 6/1999 |
| WO | WO-99/32156 | 7/1999 |
| WO | WO-99/33467 | 7/1999 |
| WO | WO-99/38493 | 8/1999 |
| WO | WO-99/39700 | 8/1999 |
| WO | WO-99/49846 | 10/1999 |
| WO | WO-99/49848 | 10/1999 |
| WO | WO-99/53901 | 10/1999 |
| WO | WO-99/59550 | 11/1999 |
| WO | WO-99/61001 | 12/1999 |
| WO | WO-99/65469 | 12/1999 |
| WO | WO-00/06152 | 2/2000 |

(56) References Cited

FOREIGN PATENT DOCUMENTS

| | | |
|---|---|---|
| WO | WO-00/09096 | 2/2000 |
| WO | WO-00/12124 | 3/2000 |
| WO | WO-00/12125 | 3/2000 |
| WO | WO-00/18374 | 4/2000 |
| WO | WO-00/27363 | 5/2000 |
| WO | WO-00/30615 | 6/2000 |
| WO | WO-00/30616 | 6/2000 |
| WO | WO-00/37050 | 6/2000 |
| WO | WO-00/40220 | 7/2000 |
| WO | WO 00/51572 | 9/2000 |
| WO | WO-00/59471 | 10/2000 |
| WO | WO-00/61108 | 10/2000 |
| WO | WO-00/71079 | 11/2000 |
| WO | WO-00/72820 | 12/2000 |
| WO | WO-01/12155 | 2/2001 |
| WO | WO-01/17546 | 3/2001 |
| WO | WO-01/21154 | 3/2001 |
| WO | WO-01/26635 | 4/2001 |
| WO | WO-01/62374 | 8/2001 |
| WO | WO-01/64164 | 9/2001 |
| WO | WO-01/80828 | 11/2001 |
| WO | WO-01/85345 | 11/2001 |
| WO | WO-01/87264 | 11/2001 |
| WO | WO-02/17883 | 3/2002 |
| WO | WO-02/22195 | 3/2002 |
| WO | WO-02/24163 | 3/2002 |
| WO | WO-02/24169 | 3/2002 |
| WO | WO-02/26324 | 4/2002 |
| WO | WO-02/43702 | 6/2002 |
| WO | WO-02/051386 | 7/2002 |
| WO | WO-02/055059 | 7/2002 |
| WO | WO 02/060411 | 8/2002 |
| WO | WO-02/072070 | 9/2002 |
| WO | WO-02/072071 | 9/2002 |
| WO | WO-02/074282 | 9/2002 |
| WO | WO-02/076446 | 10/2002 |
| WO | WO-02/080678 | 10/2002 |
| WO | WO-02/080883 | 10/2002 |
| WO | WO-02/082074 | 10/2002 |
| WO | WO-02/089773 | 11/2002 |
| WO | WO-03/024424 | 3/2003 |
| WO | WO-03/026611 | 4/2003 |
| WO | WO-03/035031 | 6/2003 |
| WO | WO-03/045330 | 6/2003 |
| WO | WO-03/045660 | 6/2003 |
| WO | WO-2004/032858 | 4/2004 |
| WO | WO-2004/056666 | 7/2004 |
| WO | WO-2004/075856 A2 | 9/2004 |
| WO | WO-2004/093795 | 11/2004 |
| WO | WO-2004/103348 | 12/2004 |
| WO | WO-2004/112747 | 12/2004 |

OTHER PUBLICATIONS

US 5,849,884, 12/1998, Woiszwillo et al. (withdrawn).

Allen et al., "Critical evaluation of acute cardiopulmonary toxicity of microspheres," *J. Nucl. Med.*, 19:1204-1208 (1987).

Allen et al., "Effects on the murine mononuclear phagocyte system of chronic administration of liposomes containing cytotoxic drug or lipid A compared with empty liposomes," *Can. J. Physiol. Pharmacol.*, 65:185-190 (1987).

Allen et al., "Large unilamellar liposomes with low uptake into the reticuloendothelial system," *FEBS Lett.*, 223:42-46 (1987).

Aquaro et al., "Macrophages and HIV infection: therapeutical approaches toward this strategic virus reservoir," *Antiviral Res.*, 55:209-225 (2002).

Avanti Polar Lipids, Inc., "Polymer and polymerizable lipids: functionalized PEG lipids," (Mar. 2003). Retrieved from the Internet: <URL: http://www.avantilipids.com>.

Avanti Polar Lipids, Inc., "Polymer and polymerizable lipids: polyethylene glycol)-lipid conjugates," (Mar. 2003). Retrieved from the Internet: <URL: http://www.avantilipids.com>.

Avanti Polar Lipids, Inc., "Synthetic products—functionalized phospholipids: lipids for conjugation of proteins/pepetides/drugs to lipsomes," (Mar. 2003). Retrieved from the Internet: <URL: http://www.avantilipids.com>.

Bender et al., "Efficiency of nanoparticles as a carrier for antiviral agents in human immunodeficiency virus-infected human monocytes/macrophages in vitro, antimicrobial agents and chemotherapy," *Antimicrob. Agents Chemother.*, 40:1467-1471 (1996).

Crowe et al., "The contribution of monocyte infection and trafficking to viral persistence, and maintenance of the viral reservoir in HIV infection," *J. Leukoc. Biol.*, 74:635-641 (2003).

Davis et al., "Pulmonary perfusion imaging: acute toxicity and safety factors as a function of particle size," *J. Nucl. Med.*, 19:1209-1213 (1978).

Duncker et al., "Effects of the pharmaceutical cosolvent hydroxypropyl-beta-cyclodextrin on porcine corneal endothelium," *Graefes Arch. Clin. Exp. Opthalmol.*, 236::380-389 (1998).

Fischer-Smith et al., "CNS invasion by CD14+/CD16+ peripheral blood-derived monocytes in HIV dementia: perivascular accumulation and reservoir of HIV infection," *J. Neurovirol.*, 7:528-541 (2001).

Graham et al., "The effects of freezing on commercial insulin suspensions," *Int. J. Pharmaceutics*, (1978).

Heiati et al., "Solid lipid nanoparticles as drug carriers: II. Plasma stability and biodistribution of solid lipid nanoparticles containing the lipophilic prodrug 3"-azido-3"-deoxythymidine palmitate in mice," *Int. J. Pharmaceutics*, 174:71-80 (1998).

Igarashi et al., "Macrophage are the principal reservoir and sustain high virus loads in *Rhesus macaques* after the depletion of CD4+ T cells by a highly pathogenic simian immunodeficiency virus/HIV type 1 chimera (SHIV): implications for HIV-1 infections of humans," *Proc. Natl. Acad. Sci. USA*, 98:658-663 (2001).

Kinman et al., "Lipid-drug association enhanced HIV-1 protease inhibitor indinavir localization in lymphoid tissues and viral load reduction: a proof of concept study in HIV-2287-infected macaques," *J. Acquir. Immune Defic. Syndr.*, 34:387-397 (2003).

Limoges et al., "Sustained antiretroviral activity of indinavir nanosuspensions in primary monocyte-derived macrophages," poster presentation, 11th Conference on Retroviruses and Opportunistic Infections, Feb. 8-11, 2004.

Lobenberg et al., "Body distribution of azidothymidine bound to hexyl-cyanoacrylate nanoparticles after i.v. injection to rats," *J. Control. Release*, 50:21-30 (1998).

Lobenberg et al., "Macrophage targeting of azidothymidine: a promising strategy for AIDS therapy," *AIDS Res. Hum. Retroviruses*, 12:1709-1715 (1996).

Moghimi et al., "Long-circulating and target-specific nanoparticles: theory to practice," *Pharmacol. Rev.*, 53:283-318 (2001).

Mroczka, "Integral transform technique in particle sizing," *J. Aerosol Sci.*, 20:1075-1077 (1989).

Nesbit et al., "In vitro and animal models of human immunodeficiency virus infection of the central nervous system," *Clin. Diagn. Lab. Immunol.*, 9:515-524 (2002).

Nottet et al., "HIV-1 entry into brain: Mechanisms for the infiltration of HIV-1-infected macrophages across the blood-brain barrier," p. 55, in Gendelman (ed.) et al., *The Neurology of AIDS*, New York: Hodder Arnold Publication (1997).

Perno et al., "Relative potency of protease inhibitors in monocytes/macrophages acutely and chronical infected with human immunodeficiency virus," *J. Infect. Dis.*, 178:413-422 (1998).

Rainbow, "Nanosuspensions in drug delivery," *Nat. Rev. Drug Discov.*, 3:785-796 (2004).

Sawchuk et al., "Investigation of distribution, transport and uptake of anti-HIV drugs to the central nervous system," *Adv. Drug Deliv. Rev.*, 39:5-31 (1999).

Schroeder et al., "Distribution of radiolabeled subvisible microspheres after intravenous administration to beagle dogs," *J. Pharm. Sci.*, 67:504-507 (1978).

Schroeder et al., "Physiological effects of subvisible microspheres administered intravenously to beagle dogs," *J. Pharm. Sci.*, 67:508-513 (1978).

(56) References Cited

OTHER PUBLICATIONS

Shrayer et al., Ceramide, a mediator of apoptosis, synergizes with paclitaxel to induce regression of the L3.6 human pancreatic carcinoma implanted in SCID mice, *J. Clin. Oncol.*, 22:2135 (2004).

Singla et al., "Paclitaxel and its formulations," *Int. J. Pharm.*, 235:179-192 (2002).

Sjostrom et al., "A method for the preparation of submicron particles of sparingly water-soluble drugs by precipitation in oil-in-water emulsions. II: Influence of the emulsifier, the solvent, and the drug substance," *J. Pharm. Sci.*, 82:584-589 (1993).

Sjostrom et al., "Preparation of submicron drug particles in lecithin-stabilized o/w emulsions I. Model studies of the precipitation of cholesteryl acetate," *Int. J. Pharm.*, 88:53-62 (1992).

Sjostrom et al., "The formation of submicron organic particles by precipitation in an emulsion," *J. Dispers. Sci. Tech.*, 15:89-117 1994.

Solas et al., "Discrepancies between protease inhibitor concentrations and viral load in reservoirs and sanctuary sites in human immunodeficiency virus-infected patients," *Antimicrob. Agents Chemother.*, 47:238-243 (2003).

Subramaniam et al., "Pharmaceutical processing with supercritical carbon dioxide," *J. Pharm. Sci.*, 86:885-890 (1997).

Volcheck et al., "Anaphylaxis to intravenous cyclosporine and tolerance to oral cyclosporine: case report and review," *Ann. Allergy Asthma Immunol.*, 80:159-163 (1998).

Von Briesen et al., "Controlled release of antiretroviral drugs," *AIDS Rev.*, 2:31-38 (2000).

Yokel et al., "Acute toxicity of latex microspheres," *Toxicol. Lett.*, 9:165-170 (1981).

Wiest et al., "Stability of esmolol hydrochloride in 5% dextrose injection," Am. J. Health-Syst Pharm. 52:716-718 (1995).

Schaaf et al., "Stability of esmolol hydrochloride in the presence of aminophylline, bretylium tosylate, heparin sodium, and procainamide hydrochloride," Am. J. Hosp. Pharm., 47: 1567-1571 (1990).

Tiwari et al., U.S. Appl. No. 11/752,086, filed May 22, 2007.

Tiwari et al., U.S. Appl. No. 11/752,037, filed May 22, 2007.

Gurinder et al., Analysis of systems failure leading to medication errors: The role of sentinel events for anesthesiologists, Anesthesiology Abstracts of Scientific Papers Annual Meeting, No. 2002, Abstract No. A-1153 (Oct. 12-16, 2002).

International Search Report for International Application No. PCT/US2008/063755, dated Mar. 12, 2009.

Lu, Goangyu, "Organic Chemical," People's Medical Publishing House, No. 1, p. 110 (Nov. 1985) (with English Translation).

* cited by examiner

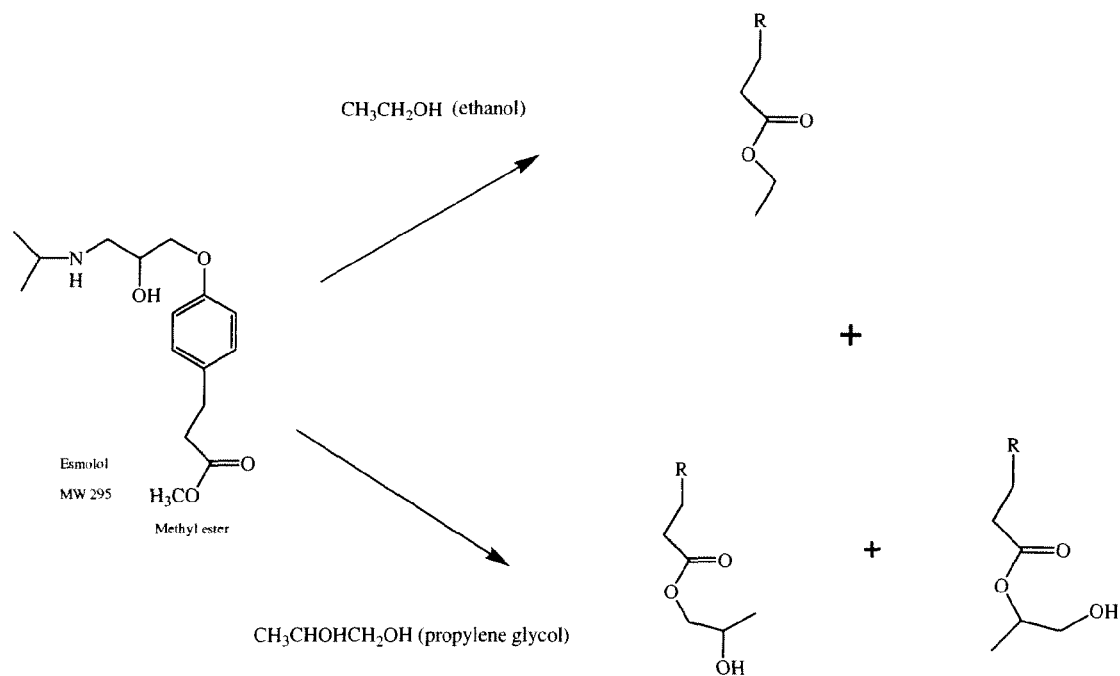
Esmolol Transesterification Reaction

MULTI-DOSE CONCENTRATE ESMOLOL WITH BENZYL ALCOHOL

BACKGROUND OF THE INVENTION

The present invention is directed to enhanced stability concentrate esmolol formulations. More specifically, the invention is directed to a concentrate esmolol formulation stabilized with benzyl alcohol. The compositions of the present invention are also suitable as multiple-dose compositions. Additionally, the present invention is directed to ready-to-use, diluted compositions made by dilution of the concentrate esmolol compositions of the present invention.

Esmolol (and its pharmaceutically acceptable salts, e.g., hydrochloride salt) and related compounds have β-adrenergic blocking activity. β-blockers are therapeutically effective agents for the treatment and prophylaxis of cardiac disorders when administered in the appropriate dosage. Esmolol, which is a short-acting β-blocker, is often times used in acute care settings to control the heart rate of a patient. The short acting property of esmolol is due to its rapid hydrolysis of the labile aliphatic methyl ester group in the blood.

Ready-to-use isotonic, and concentrate formulations, of esmolol are disclosed in U.S. Pat. Nos. 5,017,609, 6,310,094, and 6,528,540, incorporated herein by reference. Methods for making esmolol and methods for treatment or prophylaxis of cardiac disorders using such compounds are disclosed in U.S. Pat. Nos. 4,387,103, and 4,593,119, incorporated herein by reference. A current commercial esmolol concentrate formulation, covered under U.S. Pat. No. 5,017,609, comprises about 250 mg/ml of esmolol hydrochloride, 25% by volume ethanol, 25% by volume propylene glycol, 17 mg/ml sodium acetate trihydrate, and 0.715% by volume of glacial acetic acid. This composition is not intended for direct injection but for subsequent dilution with a suitable diluent.

The stability of esmolol hydrochloride {methyl3-[4-[2-hydroxy-3-(isopropylamino)propoxy]phenyl]propionate hydrochloride} in water is mediated by the rate of acid/base catalyzed hydrolysis of the labile aliphatic methyl ester group and it degrades into ASL-8123 {methyl3-[4-[2-hydroxy-3-(isopropylamino) propoxy]phenyl]propionic acid}. Ready-to-use isotonic formulations address some of the stability issues in a truly aqueous formulation and has only one degradant, ASL-8123. The current commercial concentrate formulation employs excipients (ethanol and propylene glycol) to stabilize the hydrolytic reaction, but those excipients leads to the formation of other related ester degradants. Therefore, the current commercial esmolol concentrate formulation under long term storage conditions results in the formation of ethyl and propoyl esters of esmolol in addition to ASL-8123. Furthermore the excipients (ethanol and propylene glycol) used to stabilize the current commercial esmolol concentrate formulation have been associated with potential injection site pain or irritation.

Therefore, it would be desirable to provide a stabilized concentrate esmolol composition that eliminates the formation of related ester degradants, does not include potentially irritating propylene glycol and ethanol excipients, is simpler to make than the prior art concentrate composition and, optionally, can be preserved rendering it applicable for multiple-dose use.

SUMMARY OF THE INVENTION

In one aspect of the present invention, a concentrate esmolol formulation is provided. The concentrate esmolol formulation comprises about 25-1000 mg/ml of esmolol (or pharmaceutically acceptable salts thereof), about 1 to 25% by volume of benzyl alcohol and, optionally, from about 0.005 to about 2 molar (M) of a buffering agent. The compositions are pH adjusted to between about 3.5 and about 7.0. Benzyl alcohol, typically used as a preservative, has been surprisingly found to stabilize the concentrate esmolol compositions of the present invention.

In another aspect of the present invention a ready-to-use composition and a method of dosing such composition is provided. The method comprises the steps of providing a concentrate esmolol formulation of about 25-1000 mg/ml of esmolol (or a pharmaceutically acceptable salt thereof) and 1-25% weight/volume benzyl alcohol, selecting a volume from the liquid for further dilution with a suitable diluent, followed by injection of the diluted product to the patient.

An advantage of the present invention is that, unlike prior art concentrate compositions of esmolol, the formulation does not form degredants of other related esters of esmolol.

Another advantage of the present invention is that it offers the flexibility of multiple-dose use of the formulation without microbial cross-contamination.

Another advantage of the present invention is that it reduces the potential of injection site pain/irritation contributed by propylene glycol and ethanol excipients.

Still another advantage of the present invention is that it provides sterile, concentrate esmolol compositions that contain less excipients and are simpler to make than prior art concentrates.

BRIEF DESCRIPTION OF THE DRAWING

FIG. 1 is a chemical scheme depicting the transesterification of esmolol in the presence of ethanol and propylene glycol to yield respective esters.

DETAILED DESCRIPTION OF THE INVENTION

The compositions of the present invention comprise esmolol, or pharmaceutically acceptable salts thereof, e.g., hydrochloride, and benzyl alcohol. As used herein, "esmolol" refers to esmolol free base and pharmaceutically acceptable salts thereof. The concentration of esmolol in the concentrate ranges from about 25-1000 mg/ml, and preferably is about 250 mg/ml.

As stated above, the main degradation pathway for esmolol is the hydrolysis of its aliphatic carboxy methyl ester moiety to yield ASL-8123. This degradation depends on the pH, buffer concentrations and concentration of esmolol. The current commercial esmolol concentrate formulation is stabilized by the presence of ethanol and propylene glycol. However, the historical stability data indicate that esmolol in the presence of these solvents undergoes transesterification reactions to yield ethyl and propylene glycol esters of esmolol. (See FIG. 1.)

The compositions of the present invention contain an amount of benzyl alcohol to stabilize the esmolol concentrate compositions. Although benzyl alcohol is typically used as a preservative, it has surprisingly been found to stabilize concentrate esmolol compositions of the present invention. In general, the amount of benzyl alcohol present will depend on the concentration of esmolol present. A typical range of benzyl alcohol in the compositions will be from about 1 to 25% weight/volume (w/v). Preferably, for esmolol concentrations of 250 mg/ml, benzyl alcohol will be present in a concentration of about 10% w/v.

The concentrate of present invention can also include a pharmaceutically acceptable buffer to aid in maintaining the pH in a range of from about 3.5 to about 7.0. Preferably, the pH is maintained between about 4.5 and about 5.5, more preferably between 4.9 and 5.1. Degradation of esmolol occurs most rapidly when the pH is outside the range of 4.0 to 6.0 and is most stable around a pH of about 5.0. Suitable buffers are those buffers that provide sufficient buffering capacity at the desired pH range and are pharmaceutically acceptable for injection into a patient. Examples of buffers useful in the present invention include, but are not limited to, acetate, glutamate, citrate, tartrate, benzoate, lactate, gluconate, phosphate and glycine and conjugate acids thereof. The concentration of the buffer can be from about 0.005 to about 2 M. In a preferred embodiment, the buffering agent comprises a combination of sodium acetate and glacial acetic acid. A preferred combination of buffers can include sodium acetate at from about 0.005 to about 0.3 M and glacial acetic acid at from about 0.05 to about 0.3 M.

Suitable containers for housing the esmolol concentrate are known in the art. They include vial, syringe and ampoule presentations. Containers may be fabricated of polymeric materials or from glass. Preferred polymeric containers are free of polyvinylchlorine (PVC). Preferably, the container has excellent barrier properties. A preferred container retains a moisture barrier such as glass containers or polymeric containers including barrier layers or secondary packaging. An aluminum overpouch is a preferred moisture barrier for use as secondary packaging for polymeric containers lacking a moisture barrier of their own. Preferred containers should be able to withstand terminal sterilization such as autoclaving.

The compositions of the present invention are sterile. The compositions are preferably prepared and then sterilized in their final containers by autoclaving. Alternatively, the concentrate can be aseptically prepared or terminally sterilized via autoclaving separately and then placed in sterile containers using an aseptic procedure. Typical autoclave cycles used in the pharmaceutical industry to achieve terminal sterilization of the final product are 121° C. for 15 minutes. The esmolol concentrate of the present invention can be autoclaved at a temperature ranging from 115 to 130° C. for a period of time ranging from about 5 to 40 minutes with acceptable stability. Autoclaving is preferably carried out in the temperature range of about 119 to 122° C. for a period of time ranging from about 10 to 36 minutes.

In one embodiment the concentrate is housed in a clear glass or plastic syringe and terminally sterilized. These pre-filled syringes can be provided in various volumes to permit quick and easy preparation of either small volume or large volume parental dosage by dispensing the contents of the pre-filled syringes into standard or customized, pre-filled intravenous fluid bags.

In another embodiment, the concentrate esmolol compositions of the present invention are packaged in sealed vials, preferably of type I treated glass.

The present invention is also directed to diluted, esmolol compositions made with the esmolol concentrates of the present invention. A practitioner can make a diluted concentration of esmolol with the use of a preferred diluent for infusion into the patient. Suitable diluents include diluents used by practitioners skilled in the art. Typical examples include but are not limited to, sodium chloride solutions, Ringers' or dextrose solutions. While the desired, diluted concentration of esmolol will vary depending on need, typical concentrations range from about 5 to about 25 mg/ml, and preferably 10 mg/ml of esmolol.

Suitable routes of administration for the diluted compositions of the present invention include intravenous, subcutaneous, intradermal, intramuscular, intraarticular, and intrathecal. The diluted composition is preferably administered by intravenous infusion.

The following example compositions and method of manufacture further illustrate the invention but should not be construed as limiting its scope.

Example 1

The following describes the preparation of esmolol concentrate containing 250 mg/mL of esmolol HCl and benzyl alcohol. The concentration of each ingredient of the composition is as follows:

| Ingredient | Concentration |
|---|---|
| Esmolol | 250 mg/mL |
| Sodium Acetate Trihydrate | 17 mg/mL |
| Glacial Acetic Acid | 0.00715 mL/mL |
| Benzyl Alcohol, USP | 10% w/v |
| Water for Injection, USP | Qs |

The equipment and glassware for compounding, filtering, and filling are properly washed and depyrogenated. The filter assembly, filling tube assembly, and other parts and equipment are sterilized. Eighty percent (80%) of the final volume of cool water for injection is collected in a compounding tank. Glacial acetic acid and sodium acetate are then added to the tank. Esmolol hydrochloride is weighed and added to the tank. Required quantity of the benzyl alcohol is weighed and added to the tank. The solution is stirred until all excipients are dissolved. The solution is then adjusted to pH 5.0 with sodium hydroxide or hydrochloric acid. The solution is brought to final volume with water for injection and mixed. The solution is filled in 10-mL type I treated flint ampoules and sealed. The product is the sterilized at 122° C. for 20 minutes.

Example 2

The stability of esmolol hydrochloride at 55° C. in water or water-benzyl alcohol solution is summarized in Tables 1 and 2, respectively. The stability of the formulation of Example 1 at 55 C in water is summarized in Table 3. As demonstrated by the data, the presence of benzyl alcohol greatly reduced the degradation of esmolol (Table 2). And the degradation of esmolol was further reduced when benzyl alcohol is utilized along with the buffer to maintain the pH at 5.0 (Table 3). The absence of propoyl ester degradants peak (at approximate relative retention times of 0.55 and 0.60—from an HPLC chromatogram) and ethyl ester degradant peak (at approximate relative retention times of 2.10), indicate that the present invention does not contain any of the degradants seen in the prior art current commercial esmolol concentrate formulation. Replacing ethanol and propylene glycol with benzyl alcohol eliminates the transesterification reaction and the formation of ethyl and propylene glycol ester degradants of esmolol, thereby improving the stability and safety profile of the prior art concentrate formulation.

TABLE 1

Stability of 250 mg/mL Esmolol HCL in water at 55° C.

| Time Point | pH | % Assay | % ASL-8123 | Degradants* |
|---|---|---|---|---|
| Initial | 3.86 | 101.2 | N.D | N.D |
| 1 Week | 3.33 | 87.1 | 33.8 | N.D |
| 2 Weeks | 2.43 | 54.7 | 45.7 | N.D |
| 3 Weeks | 2.30 | 26.7 | 71.7 | N.D |
| 4 Weeks | 2.24 | 14.9 | 80.7 | N.D |

*at RRT = 0.55, 0.60 and 2.10

TABLE 2

Stability of 250 mg/mL Esmolol HCL with 10% Benzyl Alcohol in water at 55° C.

| Time Point | pH | % Assay | % ASL-8123 | Degradants* |
|---|---|---|---|---|
| Initial | 3.89 | 100.7 | N.D | N.D |
| 1 Week | 3.33 | 97.1 | 10.2 | N.D |
| 2 Weeks | 2.43 | 82.9 | 16.3 | N.D |
| 3 Weeks | 2.30 | 67.3 | 31.4 | N.D |
| 4 Weeks | 2.24 | 47.0 | 50.7 | N.D |

*at RRT = 0.55, 0.60 and 2.10

TABLE 3

Stability of 250 mg/mL Esmolol HCL with 10% Benzyl Alcohol in buffered water at 55° C.

| Time Point | pH | % Assay | % ASL-8123 | Degradants* |
|---|---|---|---|---|
| Initial | 4.60 | 106.9 | 1.24 | N.D |
| 1 Week | 4.60 | 101.2 | 2.70 | N.D |
| 4 Weeks | 4.60 | 95.5 | 9.61 | N.D |

*at RRT = 0.55, 0.60 and 2.10

Although the present invention has been described by reference to certain preferred embodiments, it should be understood that the preferred embodiments are merely illustrative of the principles of the present invention. Therefore, modifications and/or changes may be made by those skilled in the art without departing from the true spirit and scope of the invention as defined by the appended claims.

What is claimed is:

1. A concentrate esmolol composition comprising:
   a) about 25 to about 1000 mg/ml of esmolol; and
   b) from about 1 to about 25% w/v of benzyl alcohol;
   wherein the composition has a pH of about 3 to about 7,
   wherein the concentrate esmolol composition is more stable than a comparable control esmolol composition having the same esmolol concentration and pH but excluding benzyl alcohol.

2. The composition of claim 1, further comprising a buffering agent.

3. The composition of claim 2, wherein the buffering agent comprises at least one of acetate, glutamate, citrate, tartrate, benzoate, lactate, gluconate, phosphate and glycine and conjugate acids thereof.

4. The composition of claim 3, wherein the buffering agent comprises sodium acetate and acetic acid.

5. The composition of claim 2, wherein the buffering agent is present in an amount of from about 0.005 to about 2 M.

6. The composition of claim 1 comprising:
   a) about 250 mg/mL esmolol;
   b) about 10% w/v of benzyl alcohol; and
   c) about 0.1 M acetate.

7. The composition of claim 1 comprising:
   a) about 50 mg/mL esmolol;
   b) about 2% w/v benzyl alcohol; and
   c) about 0.1 M acetate.

8. A method of dosing a patient with an esmolol composition comprising the steps of:
   a) providing a volume of a first composition which is a concentrate esmolol composition according to claim 1;
   b) diluting the volume of the first composition with a volume of a second composition, the second composition comprising a pharmaceutically acceptable diluent for parenteral administration, to form a ready-to-use composition;
   c) selecting a volume of the ready-to-use composition; and
   d) dosing a patient with the volume of ready-to-use composition.

9. The method of claim 8, wherein the first composition further comprises a buffering agent.

10. The method of claim 9, wherein the buffering agent is present in a concentration of from about 0.005 to 2 M.

11. The method of claim 9, wherein the first composition comprises about 0.1 M acetate:
    a) about 50 mg/mL esmolol;
    b) about 2% w/v benzyl alcohol; and
    c) about 50 mg/mL esmolol.

12. The method of claim 9, wherein the first composition comprises:
    a) about 250 mg/mL esmolol;
    b) about 10% w/v of benzyl alcohol; and
    c) about 0.1 M acetate.

13. The method of claim 11, wherein the buffering agent comprises sodium acetate and acetic acid.

14. A concentrate esmolol composition consisting of:
    a) about 25 to about 1000 mg/ml of esmolol;
    b) from about 1 to about 25% w/v of benzyl alcohol;
    c) from about 0.005 to about 2 M of a buffering agent; and
    d) water;
    wherein the composition has a pH of about 3 to about 7, and wherein the concentrate esmolol composition is more stable than a comparable control esmolol composition having the same esmolol concentration and pH but excluding benzyl alcohol.

* * * * *